(12) United States Patent
Carlin et al.

(10) Patent No.: US 7,717,624 B2
(45) Date of Patent: May 18, 2010

(54) CONNECTORS FOR MULTI FIBER OPTICAL PROBES

(75) Inventors: Donald B. Carlin, Pennington, NJ (US); Gerard A. Alphonse, Princeton, NJ (US); Mahesh Ajgaonkar, Buda, TX (US); Alexandru Paunescu, Clinton, NJ (US)

(73) Assignee: Medeikon Corporation, Ewing, NJ (US)

( * ) Notice: Subject to any disclaimer, the term of this patent is extended or adjusted under 35 U.S.C. 154(b) by 620 days.

(21) Appl. No.: 11/736,265

(22) Filed: Apr. 17, 2007

(65) Prior Publication Data

US 2008/0262442 A1   Oct. 23, 2008

(51) Int. Cl.
*G02B 6/00* (2006.01)
*G02B 6/36* (2006.01)
*A61M 5/00* (2006.01)

(52) U.S. Cl. .............................. 385/53; 385/70; 385/74; 604/264

(58) Field of Classification Search .................. 385/53, 385/56, 70–74, 15, 27, 39, 33, 117, 119, 385/147; 604/264
See application file for complete search history.

(56) References Cited

U.S. PATENT DOCUMENTS

| 4,176,662 A * | 12/1979 | Frazer ........................ 600/114 |
| 5,774,610 A | 6/1998 | O'Rourke et al. |
| 6,445,939 B1 | 9/2002 | Swanson et al. |
| 7,647,092 B2 * | 1/2010 | Motz et al. .................. 600/478 |
| 2008/0002927 A1* | 1/2008 | Furnish ....................... 385/12 |
| 2008/0267562 A1* | 10/2008 | Wang et al. ................... 385/31 |
| 2009/0175576 A1* | 7/2009 | Tang ........................... 385/31 |
| 2009/0285538 A1* | 11/2009 | Marple ....................... 385/115 |

* cited by examiner

*Primary Examiner*—Akm E Ullah
(74) *Attorney, Agent, or Firm*—Pepper Hamilton LLP

(57) ABSTRACT

Connectors and linking components for a guidewire probe having multiple optical emitting fibers and methods of making connectors and linking components for guidewire probes having multiple optical emitting fibers are described herein.

18 Claims, 7 Drawing Sheets

CONNECTORS FOR MULTI FIBER OPTICAL PROBES

BACKGROUND

Stents are expandable devices inserted into arteries via angioplasty techniques that keep a blood vessel open. They are typically open tubular structures having, for example, struts and ribs that allow expansion when an interiorly placed balloon is inflated. The stents are typically made of metal although other materials are possible, and are designed to be inflated with sufficient pressure to make close contact with the wall of the lumen in the artery being treated. Manufacturer recommended pressures for expansion of standard stents are typically in the range of from 4 to 16 atmospheres.

Current clinical practice is to position a balloon and stent in the required location by observation, for example, using angiographic x-ray techniques. The balloon is typically filled with a solution of saline and x-ray contrast agent. The angiogram presents a one-dimensional cross-sectional view of the artery with relatively poor spatial resolution, which is commonly the case, as the lumen of an artery does not necessarily have a circular cross-section, especially in atherosclerotic sections where it is likely to be an irregular shape. Although the physician may view the artery from more than one angle, the information provided by angiography is limited and insufficient to provide an accurate assessment of the size to which the stent should be inflated.

Angiography is also used in current clinical practice to determine the degree to which an artery is narrowed. Narrowing of the artery is called stenosis and is illustrated in FIG. 1A. Stenosis is caused by the buildup of plaque 14 commonly referred to as lesions on an interior area of an artery wall 10. This in turn decreases a cross-section of the lumen 16 through which blood flows 12. In FIG. 1A, the narrowing caused by an atherosclerotic plaque 14 is of the order of 70% in the longitudinal view and, as such, would likely be treated with balloon angioplasty and stent placement. The cross-sectional view of FIG. 1A, shown at lower inset, illustrates the irregularly shaped lumen 16. As illustrated, plaques 14 commonly form with increased frequency at or very near to bifurcations of the artery 18.

In current, practice, the cardiologist estimates the degree of narrowing as compared to the expected dimension of an open lumen. Based on this estimation, the cardiologist then determines whether an angioplasty or coronary artery bypass graft (CABG—bypass surgery) is required to improve blood flow. Such stenotic lesions as plaques 14 are commonly treated using balloon angioplasty, as illustrated in FIG. 1B. A balloon catheter 22 includes a dilation balloon 20 attached to a guidewire 24 to navigate through the artery. The dilation balloon 20 is inserted at the area of the lesion 14 and inflated to increase the luminal size 16. Following dilation, stents which may be deployed by the use of the balloon catheter 22 are commonly placed at the site of the lesion to prevent stenosis at a later time (restenosis).

As known in the field, accurate stent expansion is critical to the success of an angiography procedure. For example, the over-expansion of a stent can cause rupture of the blood vessel. Conversely, under-expansion of a stent leaves areas or gaps between a stent structure and lumen wall which can lead to thrombosis.

Accordingly, there is a need for a device, system, and method which provide for accurate measurement of the dimensions of a luminal space of an artery thereby allowing for the determination of the size to which a stent should be expanded. There is also a need for combining a device for determining the location of a lesion with a means for deploying a sent. Such a combined device requires connectors which allow the locating device to identify a lesion, disconnect from an instrument box allowing a secondary device to be slid over the locating device so that the secondary device may act on the lesion, for example, deploy a stent, and reconnect to the instrument box to allow observation of the deployed stent.

SUMMARY

The invention described herein is generally directed to an optical probe including a guidewire having a plurality of optical emitting fibers, a linking component having a plurality of optical fiber feed lines corresponding to each of the plurality of optical emitting fibers, and a connector affixed to the distal end of the linking component and engagably attached to the proximal end of the guidewire. The guidewire may have an angled proximal end wherein light enters the plurality of optical emitting fibers and a distal end wherein light from the plurality of optical emitting fibers illuminates a target. The linking component may generally have a proximal end and an angled distal end wherein the angled distal end of the linking component corresponds with the angled proximal end of the guidewire and wherein each of the plurality of optical fibers is aligned with a corresponding optical fiber feed line at a mating interface such that the connector locks a mating interface in place.

In some embodiments no part of the connector affixed to the guidewire exceeds a diameter of the guidewire, and in others, the plurality of optical emitting fibers and optical fiber feed lines at the mating interface may have a spatial and angular orientation that allows self alignment of each optical emitting fiber to its corresponding optical fiber feed line. In certain embodiments, the connector may further include an attachment or appendage.

The plurality of optical emitting fibers and the optical fiber feed lines may be any optical fiber or waveguide, such as, but not limited to, single mode fibers, multi-mode fibers, and combinations thereof, and in particular embodiments, the plurality of optical emitting fibers and the optical fiber feed lines are made up of the same type of fiber. In some embodiments, the mating interface may further include a fluid having a refractive index about equal to a refractive index of the plurality of optical emitting fibers and optical fiber feed lines.

Other embodiments of the invention include an optical probe including a guidewire made-up of at least one optical emitting fiber for observing a target, a linking component connecting, and disconnecting the guidewire to a light source, and a second device inserted over the guidewire that extends the length of the guidewire wherein the guidewire allows the second device to be positioned in the target area. In some embodiments, the second device may deliver treatment to diseased tissue observed by the at least one optical emitting fiber, and in certain embodiments, the second device may include a balloon. In still other embodiments, the second device may further include a balloon and a stent.

The linking component, of some embodiments, may include a connector affixed to an end of the linking component for connecting and disconnecting the linking component and the guidewire and locking the guidewire and linking component in place.

The invention further includes a method for using an optical probe including the steps of inserting a guidewire including a plurality of optical emitting fibers into a lumen such that a distal end of the guidewire is inserted into the lumen and a proximal end of the guidewire remains outside of the lumen, connecting the guidewire to a light source and a processing device by a linking component having a plurality of optical fiber feed lines corresponding to each of the plurality of optical emitting fibers, determining a position of diseased tissue or target position within the lumen, maintaining a position of the guidewire in close proximity to the target position, disconnecting the guidewire and the linking component, inserting a second device over the guidewire while the position of the guidewire is maintained in close proximity to the target position, utilizing the second device, and reconnecting the guidewire and the linking component.

In some embodiments, the linking component may have a proximal end and a distal end wherein the proximal end of the linking component engagably attaches to the proximal end of the guidewire. In other embodiments, the component may further include a connector for reversibly connecting the guidewire to the component at a mating interface wherein the plurality of optical emitting fibers and the corresponding plurality of optical fiber feed lines are ground and polished to an angle such that a spatial and angular orientation of the mating interface allows self alignment of each optical fiber feed line to a corresponding optical emitting fiber.

In various embodiments, the second device may be a sleeve or a balloon, and the second device may further include a stent. Utilizing the second device may include deploying a stent in the target position, and in some embodiments, the method may further include inspecting placement of the stent using the guidewire following deployment of the stent to ensure proper placement and deployment.

The invention also includes a method for making an optical probe including the steps of assembling a plurality of optical emitting fibers in a hollow guidewire such that the combined length of each optical fiber is at least equal to the total of the length of a guidewire probe and a linking component, and slicing the guidewire at an angle wherein the angle allows the optical emitting fibers to be realigned and assume its original length.

The method may further include polishing the sliced optical emitting fibers and/or fixing a connecter to the linking component at an interface between the guidewire probe and the linking component.

The invention also includes an optical probe for stent deployment including a guidewire having at least one optical emitting fiber for observing a target, a linking component engagably attaching the guidewire to a light source, a connector affixed to an end of the linking component opposite the light source and engagably attached to the guidewire, a second device reversibly fitting over the guidewire wherein the guidewire positions the second device in an area in close proximity to the target, and a stent attached to the second device to be deployed to the target. In some embodiments, the stent may be located at an end of the second device. In other embodiments, the linking component may include at least one optical fiber feed line corresponding to the at least one optical emitting fiber and having a proximal end and an angled distal end wherein the angled distal end of the linking component corresponds with an angled proximal end of the guidewire. In particular embodiments, each of the plurality of optical fibers may be aligned with a corresponding optical fiber feed line at a mating interface.

The invention also includes a connector for a multi-fiber optical probe including a guidewire having a plurality of optical emitting fibers and an angled proximal end wherein light enters the plurality of optical emitting fibers and a distal end wherein light from the plurality of optical emitting fibers illuminates a target at the distal end, a linking component having a plurality of optical fiber feed lines corresponding to each of the plurality of optical emitting fibers and a proximal end and an angled distal end wherein the angled distal end of the linking component corresponds with the angled proximal end of the guidewire and wherein each of the plurality of optical fibers is aligned with a corresponding optical fiber feed line at a mating interface, and a connector affixed to the distal end of the linking component and engagably attached to the proximal end of the guidewire wherein the connector locks the mating interface in place.

DESCRIPTION OF DRAWINGS

For a better understanding of the disclosure and to show how the same may be carried into effect, reference will now be made to the accompanying drawings. It is stressed that the particulars shown are by way of example only and for purposes of illustrative discussion of the preferred embodiments of the present disclosure only, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings making apparent to those skilled in the art how the several forms of the invention may be embodied in practice. In the accompanying drawings.

"The file of this patent contains at least one drawing executed in color. Copies of this patent with color drawing(s) will be provided by the Patent and Trademark Office upon request and payment of necessary fee."

DETAILED DESCRIPTION

Before the present devices, systems and methods are described, it is to be understood that this invention is not limited to the particular processes, devices, or methodologies described, as these may vary. It is also to be understood that the terminology used in the description is for the purpose of describing the particular versions or embodiments only, and is not intended to limit the scope of the present disclosure which will be limited only by the appended claims.

It must also be noted that as used herein and in the appended claims, the singular forms "a", "an", and "the" include plural reference unless the context clearly dictates otherwise. Thus, for example, reference to an "artery" is a reference to one or more arteries and equivalents thereof known to those skilled in the art, and so forth. Unless defined otherwise, all technical and scientific terms used herein have the same meanings as commonly understood by one of ordinary skill in the art. "Optional" or "optionally" means that the subsequently described structure, event or circumstance may or may not occur, and that the description includes instances where the event occurs and instances where it does not.

The term "plaque" may be taken to mean any localized abnormal patch on a body part or surface. In regard to arterial plaques, plaques may be fatty deposits on the inner lining of an arterial wall and are characteristic of atherosclerosis. The plaque may be an abnormal accumulation of inflammatory cells, lipids and a variable amount of connective tissue within the walls of arteries. In part, embodiments of this invention are directed to the detection and treatment of plaques.

Although any methods and materials similar or equivalent to those described herein can be used in the practice or testing of embodiments of the present disclosure, the preferred methods, devices, and materials are now described. Nothing herein is to be construed as an admission that the invention is not entitled to antedate such disclosure by virtue of prior invention.

The invention presented herein is generally directed to connectors for a device or sensor having multiple optical emitting fibers, methods for making connectors for such a device, and methods for using a connector for such a device, for example, in deployment of a stent in an arterial lumen.

Figure 1A:
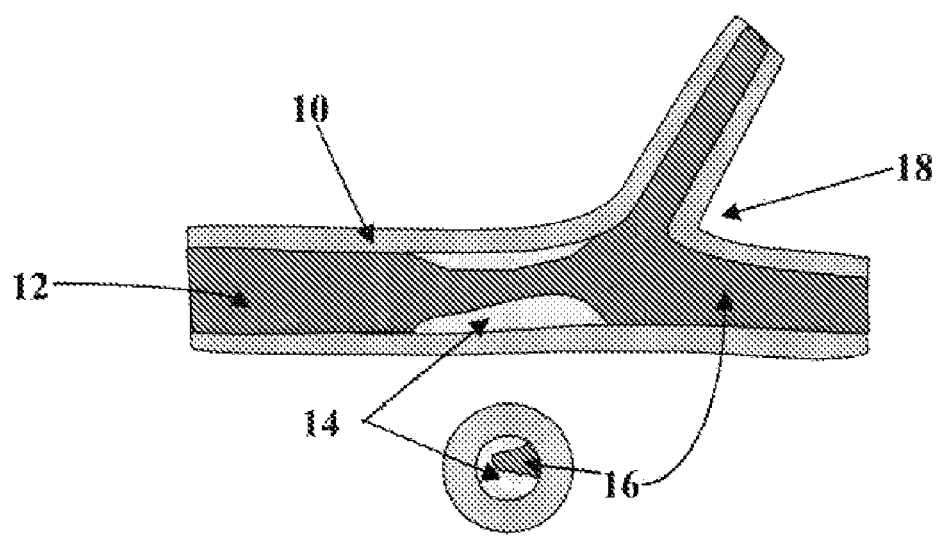
FIG. 1A shows a narrowing of an artery caused by an atherosclerotic plaque.
Figure 1B:
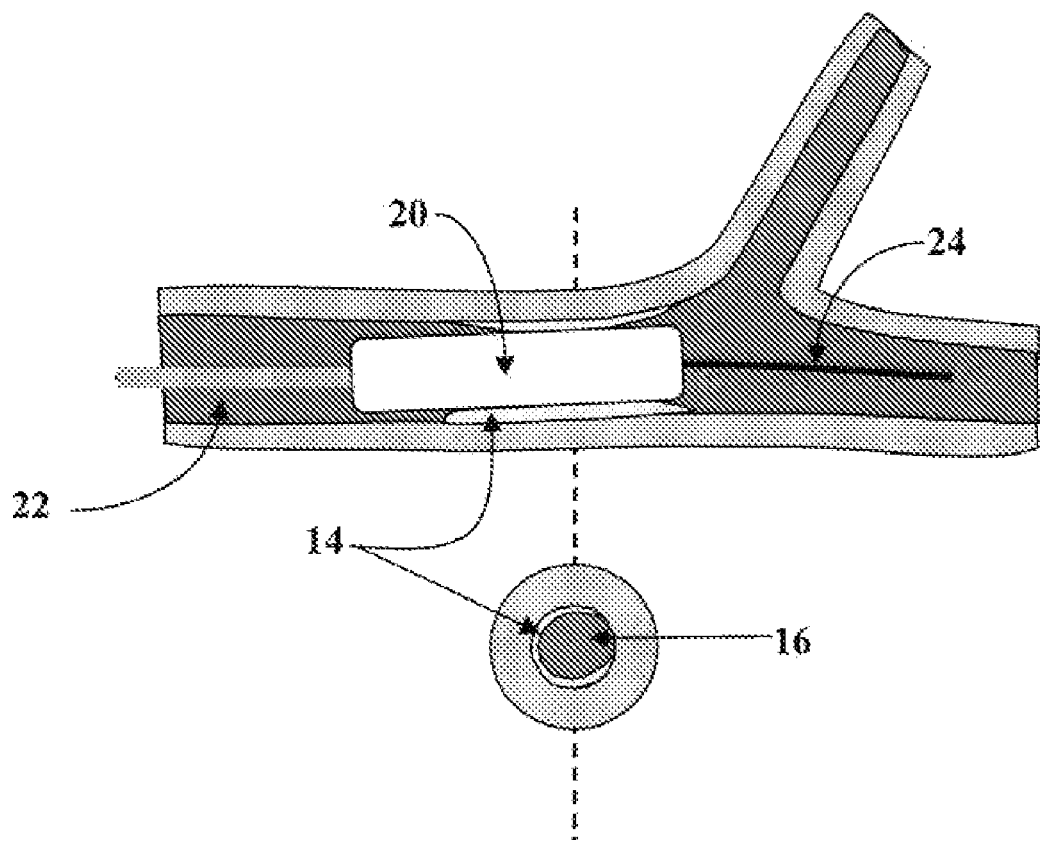
FIG. 1B shows a stenotic lesion being treated with a balloon catheter.
Figure 2:
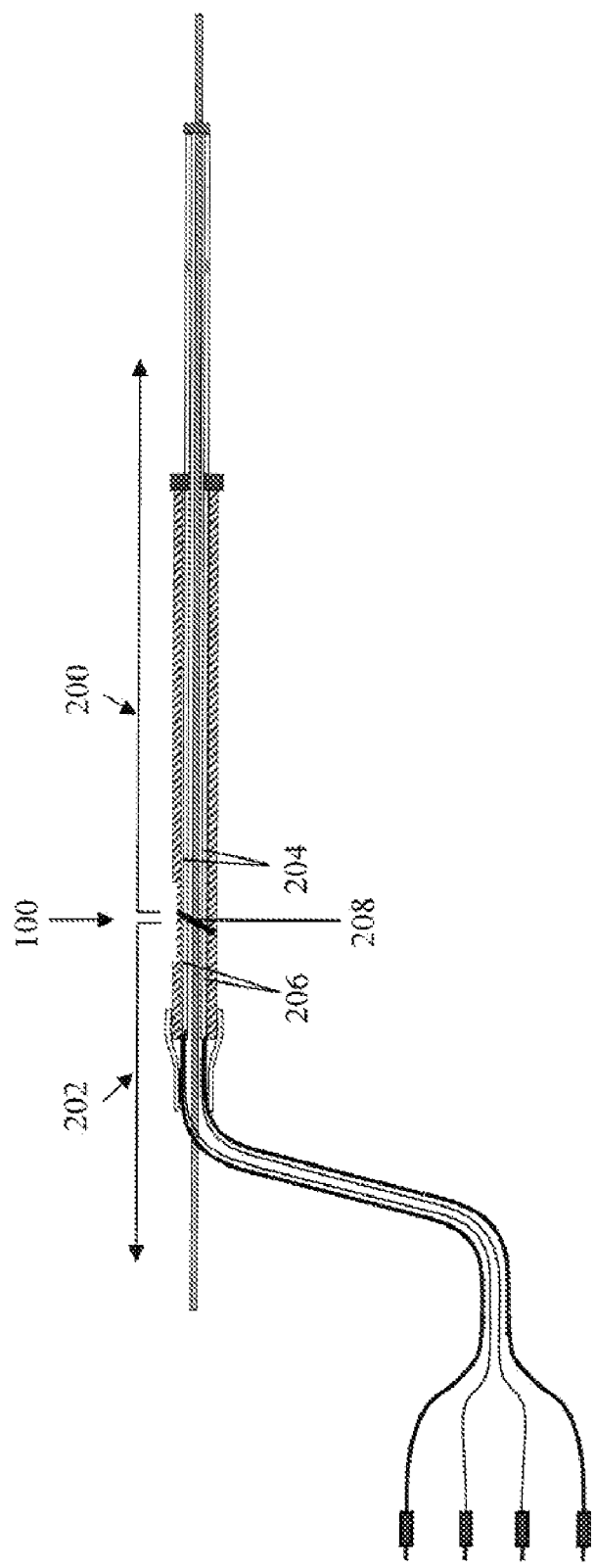
FIG. 2 shows a guidewire probe containing multiple optical emitting fibers connected to a linking component connector in accordance with the present invention.

As illustrated in FIG. 2, the connector 100 of the invention generally describes a means by which the separate components of an optical probe meet at a mating interface 208 and may include a guidewire probe 200 having a plurality of optical emitting fibers 204 and a linking component 202 having optical fiber feed lines 206 corresponding to each of the plurality of optical emitting fibers 204 of the guidewire probe 200.

The linking component 202, as illustrated in FIG. 2, may operably link the guidewire probe 200 to a power source and/or a detector. The plurality of optical emitting fibers 204 in the guidewire probe 200 and corresponding optical fiber feed lines 206 in the linking component 202 may meet at a mating interface 208 that has been cut and polished at an angle which, in some embodiments, may be at least greater than about 3° up to about 20° and, in particular embodiments, about 8° as measured from a plane perpendicular to an axial centerline of the guidewire probe. Without wishing to be bound by theory, the angled interface 208 may provide a two-fold advantage over an interface cut perpendicularly to an axial centerline of a guidewire. First, the angled interface 208 provides a low reflection junction between the plurality of optical emitting fibers 204 and the optical feed lines 206 reducing back-reflection in the optical emitting fiber. Second, the angled interface 208 allows for self-alignment of the plurality of optical emitting fibers 204 with the optical feed lines 206 because the guidewire probe 200 and the linking component 202 can be mated only at the angle of the angled interface 208. Therefore, each of the plurality of optical emitting fibers 204 may be automatically mated with its corresponding optical fiber feed line 206.

Figures 3A, 3B:
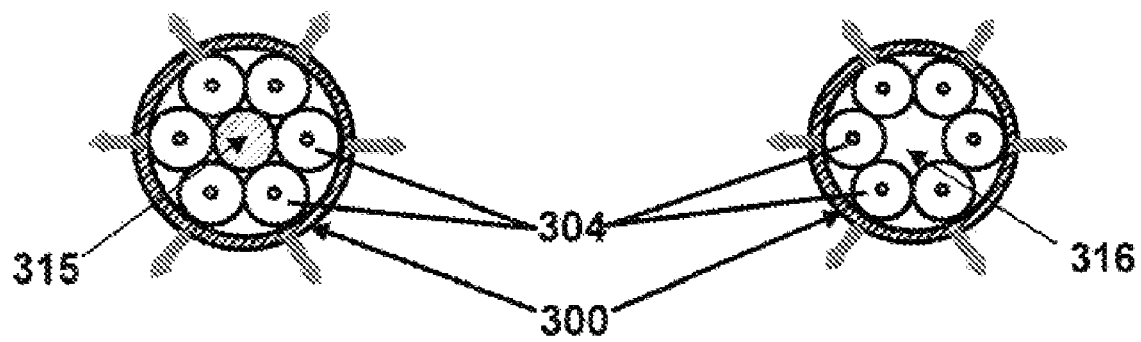
FIG. 3A shows an arrangement of optical emitting fibers around a central wire.
FIG. 3B shows an arrangement of optical emitting fibers around a hollow cavity.

FIGS. 3A and 3B illustrate embodiments of arrangements of optical emitting fibers 304 in a guidewire 300. In embodiments, six optical emitting fibers 304, for example, six 80-micron single mode fibers, may be arranged around an internal perimeter of a guide wire 300, such as, for example, an 1F (1-French) guidewire. Light may be deflected radially away from central axis of the guidewire 300 as indicated by the arrows to illuminate the walls of a lumen. In some embodiments, a central wire or tube 315 may be located in the center of the guidewire 300 and the optical emitting fibers 304 may be arranged around the central wire or tube 315 as illustrated in FIG. 3A. In alternate embodiments, the central wire or tube 315 may be absent leaving the center 316 of the guidewire hollow as illustrated in FIG. 3B.

Figure 4:
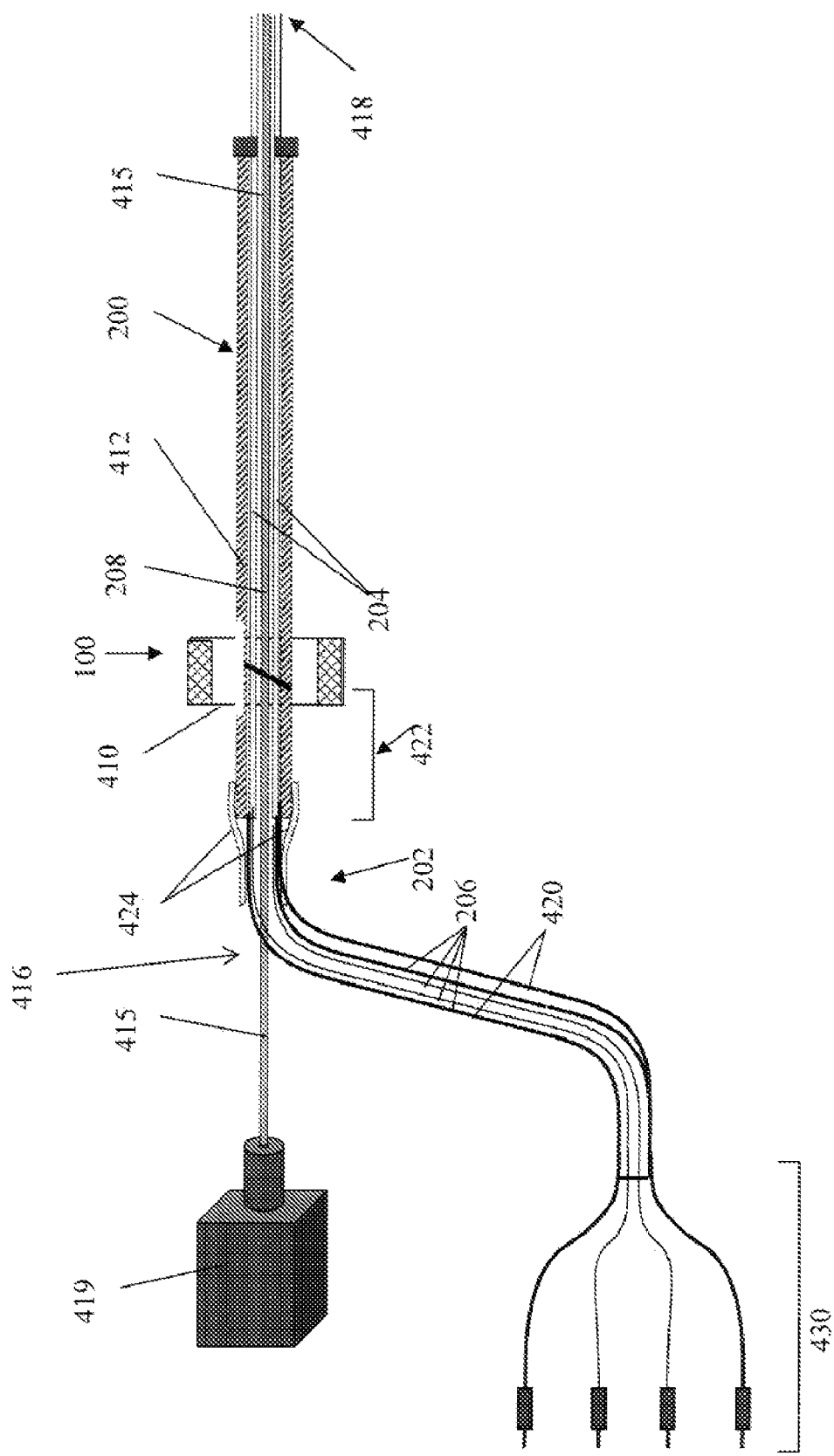
FIG. 4 shows a guidewire probe containing multiple optical emitting fibers and a linking component having a central wire or tube connected to an actuator or pump.

As illustrated in FIG. 4 in some embodiments, a locking mechanism or knob 410 may be placed around at least a portion of the connector 100 to facilitate a secure connection between the guidewire probe 200 and the linking component 202. In particular embodiments, no part of the guidewire probe 200 or the connector 100 may exceed the diameter of the guidewire. For example, the guidewire may have a notch 412 or an internal or embedded appendage that facilitates alignment or locking, but no part of the guidewire probe 200 or appendage attached to the guidewire probe 200 may exceed the diameter of the guidewire. By limiting the diameter of the guidewire probe 200 and eliminating appendages that may increase the diameter of the guidewire probe 200, secondary devices or probes may be easily placed over the guidewire probe 200 during use. Therefore, the need to reconfigure or remove the guidewire probe 200 from the lumen being examined during examination is eliminated.

In other embodiments illustrated in FIG. 4, the guidewire probe 200 may further include a central wire or tube 415 around which the optical emitting fibers 204 are arranged. The linking component 202 in such embodiments may further include a hole or opening 416 through which the central guidewire or tube 415 may pass. The central wire or tube 415 may remain accessible to the user of the guidewire probe, and the user may manipulate the central wire or tube to affect a change in the guidewire probe 200 or to operate an optical probe head 418 attached to the guidewire probe 200. For example, the user may use the central guidewire 415 to manipulate the optical probe head 418 or cause the guidewire probe 200 to bend. In further embodiments, the central wire of tube 415 may be attached to another device 419 such as, for example, an actuator, controller, air compressor and the like, winch mechanically manipulates the central wire or tube or an optical probe head 418 attached to the distal end of the guidewire probe 200.

In still other embodiments, the linking component 202 may further include a flexible boot or jacket 420 encapsulating the optical feed lines 206 but allowing greater flexibility of the optical feed lines 206 than the guidewire probe 200. In such embodiments, a guidewire section of the linking component 422 may consist of a section of guidewire identical to that of the guidewire probe 200 in which the plurality of optical emitting fibers are arranged as in the guidewire probe 200. The guidewire section of the linking component 422 may extend from the angled interface 208 to some distance past a locking component 410. The optical feed lines 206 may extend past the end of the guidewire section of the linking component 422 and may be encapsulated by the flexible boot or jacket 420 which extends from, and may be continuous with, the guidewire section of the linking component 422. In some embodiments, the interface between the guidewire section of the linking component 422 and the flexible boot or jacket 420 may further include a strain relief boot 424 that may be connected to both the guidewire section 422 and the flexible boot or jacket 420. The strain relief boot 424 may consist of a substance having stiffness greater than the flexible boot or jacket 420 but less than the guidewire section of the linking component 422 and may provide support for the optical feed lines 206 during bending to ensure that the optical emitting fibers do not bend excessively causing distortion of the signal or breakage of the optical emitting fibers. The flexible boot or jacket 426 may extend from the interface between the guidewire section of the linking component 422 to the proximal most part of the optical feed lines 206 extending beyond the end of the flexible boot or jacket 420 at a linking component terminus 430 of the linking component 202.

Figure 5:
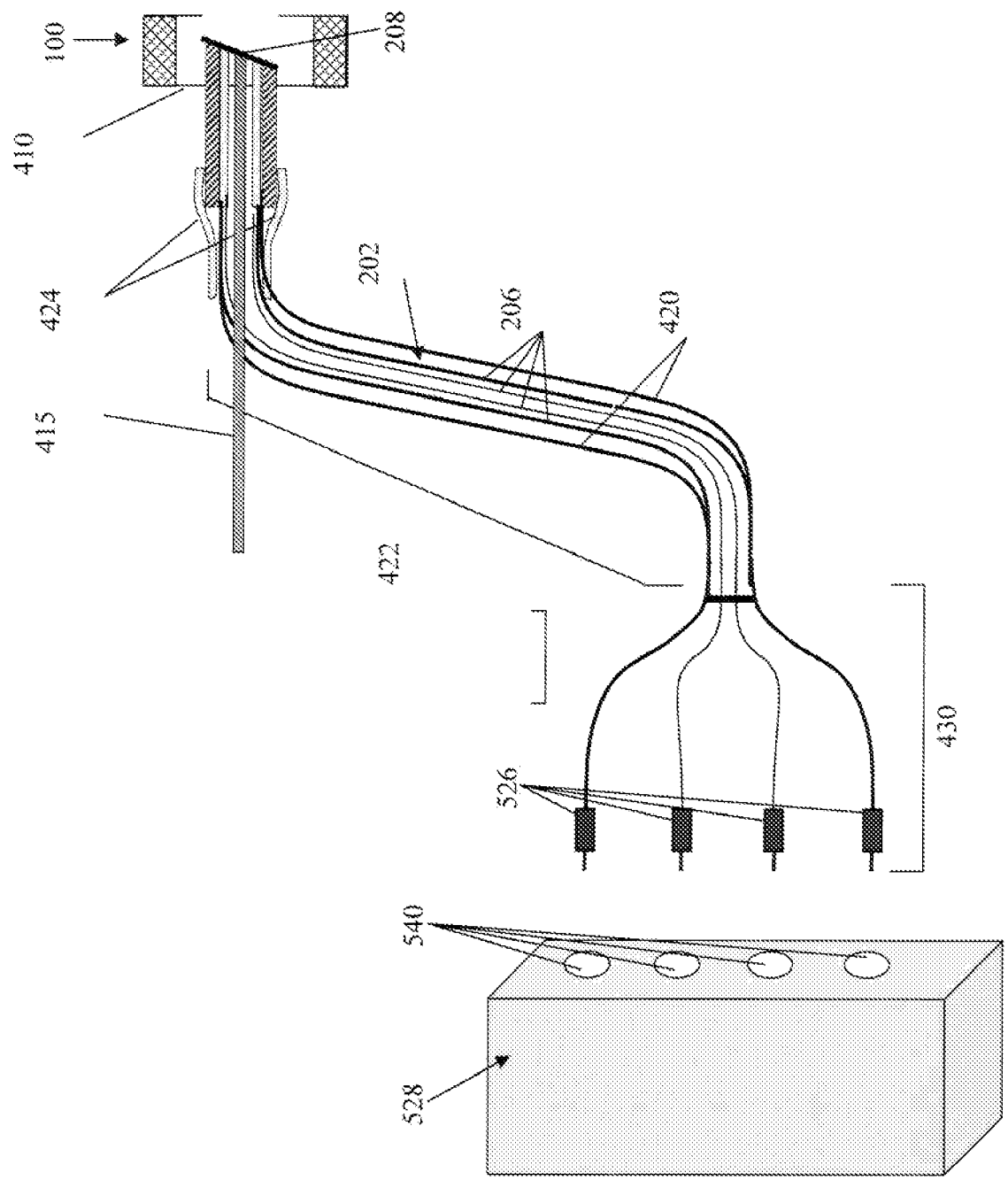
FIG. 5 shows an expanded view of a linking component with multiple optical feed line connectors.

In embodiments as illustrated in FIG. 5, the optical feed lines 206 of the linking component 202 may terminate at the end opposite the interface 208 at a linking component terminus 430 in a single connector 100 or series of optical feed line connectors 526 that reversibly attach the linking component to an instrument box 528 or, in some embodiments, a light source or detector.

Figure 6:
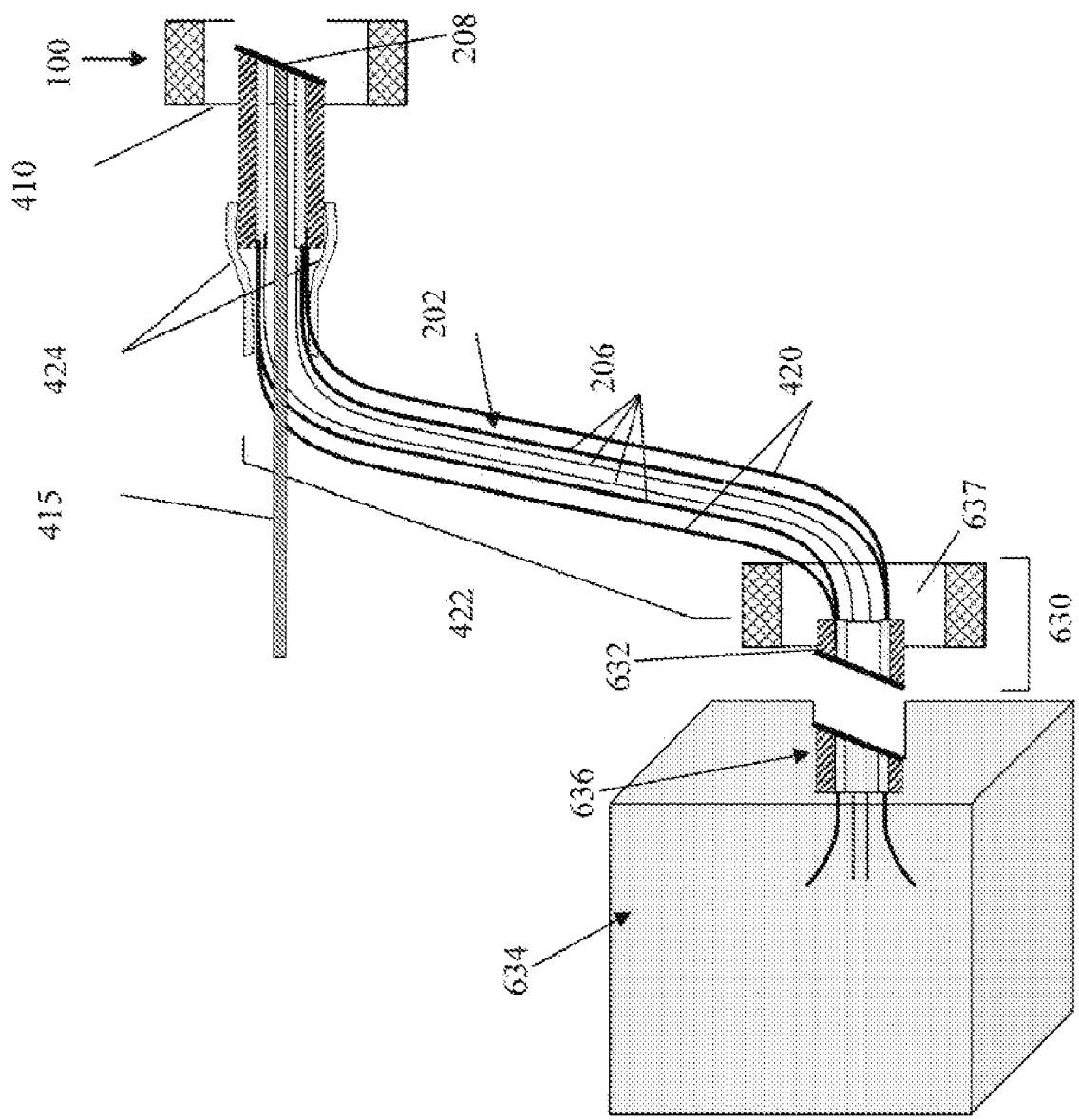
FIG. 6 shows an expanded view of a linking component with a single optical feed line connector.

An instrument box 528 may contain an instrument box connector 540 for each optical feed line connector 526, or a single instrument box connector for a combined optical fiber feed line connector wherein individual connectors for each optical feed line 206 are combined into a single connector (See FIG. 6). The connectors 526 may be any type of connector known in the art that may be used in a device including optical emitting fibers.

In an embodiment illustrated in FIG. 6, the linking component 202 may terminate at the end opposite die interface 208 in a single optical connector 630 that is similar to that by which the guidewire probe 200 is attached to the linking component 202 as depicted in FIG. 2. In such embodiments, a section of guidewire 632 having the optical emitting fibers arranged as in the guidewire probe may be attached to the optical connector 630 and the section of guidewire 632 may be cut at an angle that precisely matches a pre-aligned fiber bundle 636 in an instrument box 634. Therefore, each of the optical feed lines 206 of the linking component 202 may automatically be mated with the corresponding optical emitting fiber in the pre-aligned fiber bundle 636. The optical connector 630 may further include a locking mechanism or knob 637 that attaches the linking component 202 to an instrument box 634 and may secure and hold the connection of the optical feed lines 206 of the linking component 202 to the corresponding optical emitting fiber in the pre-aligned fiber bundle 636 in position.

Figure 7:
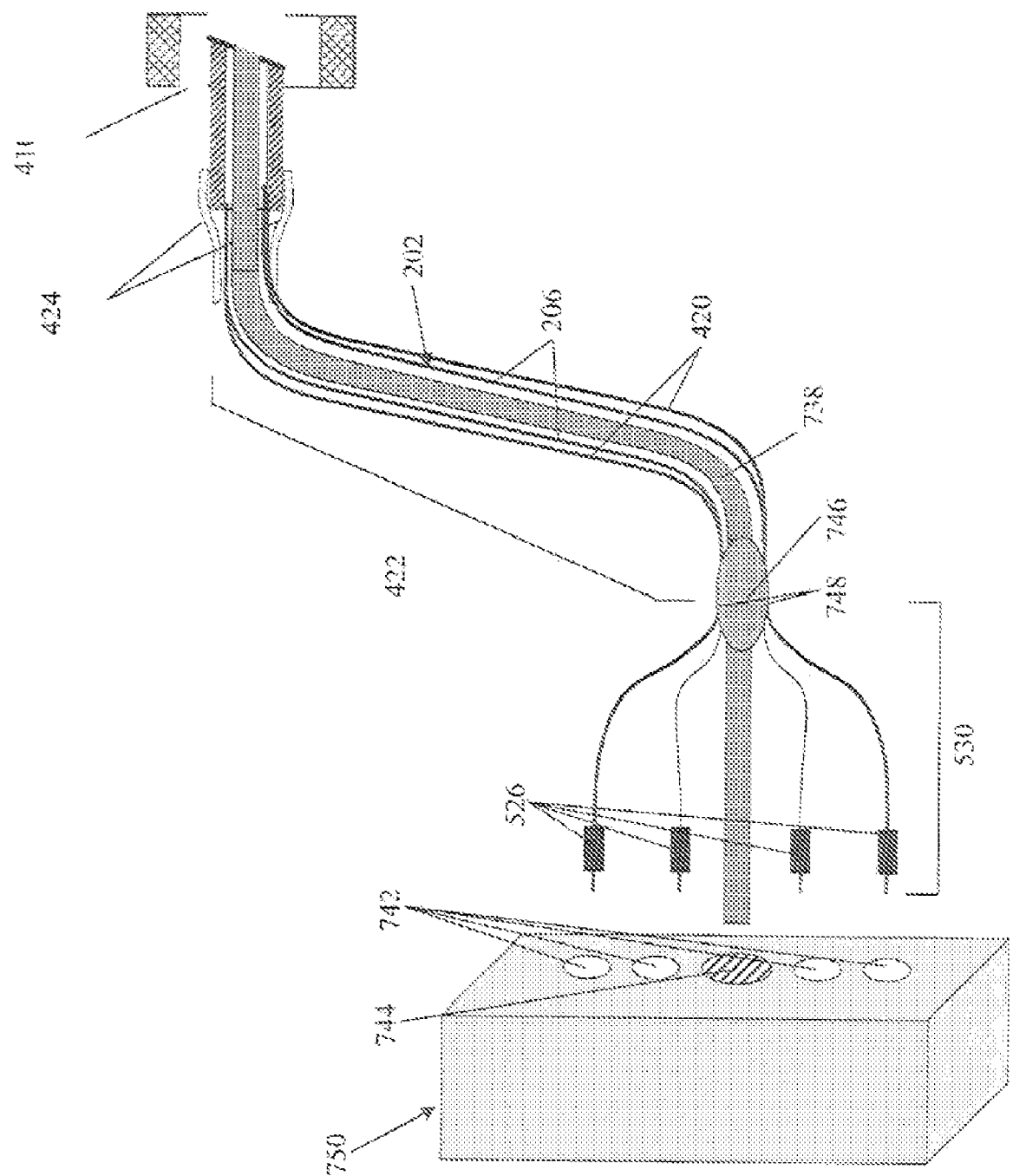
FIG. 7 shows an expanded view of a linking component with multiple optical feed line connectors and a hollow central tube.

In various embodiments, the central wire or tube 415 may pass through the flexible jacket or boot 420, for example, through a hole in the flexible boot or jacket 416 as indicated in FIGS. 4, 5 and 6. Therefore, the central wire or tube 415 may remain accessible to the user or a manipulation device 419 as depicted in FIG. 4. In other embodiments, the central hollow feed tube 738 may be contained in the flexible jacket or boot 420 with the optical feed lines 206 as illustrated in FIG. 7. The linking component 202, of such embodiments, may contain a central hollow feed tube 738 that delivers a substance such as air or a liquid to the central tube 415 of the guidewire probe 200 to initiate manipulation of the guidewire probe, for example, inflating an optical probe head 418 as shown in FIG. 4. In some embodiments, the hollow central tube 738 and the optical feed lines 202 may terminate at the linking component terminus 530 in individual connectors 526 which may be inserted into an instrument box 750, or in other embodiments, the hollow central tube 738, and the connectors 526 may be combined into a single connector. In other embodiments, a seal 746 may be formed at the terminal end of the flexible jacket or boot 420. The seal 746 may act to seal the flexible jacket or boot 420 from the environment and consolidate the central hollow feed tube 738 and the optical feed lines 206, and may protect the optical feed lines 206 from leaks of the substance moving through the central hollow feed tube 738. In other embodiments, the seal 746 may further include a valve that may stop the flow of, for example, air or fluid, into the guidewire probe, or release the air or fluid from the central hollow feed tube 738.

The instrument box connectors 750 of various embodiments may be arranged in any order, for example, as illustrated in FIG. 7, optical feed line connectors 742 may flank a central pump insert 744 that is designed to connect with the hollow central tube 738. In some embodiments, the optical feed lines 206 may connect to an instrument box that is separate from the pump into which the central hollow tube is connected.

The linking component of embodiments may further include a handle or grip. A handle or grip may be made of any material known in the art such as, for example, a polymer, cloth, or cloth tape which may allow the user to manipulate the guidewire probe and/or the linking component easily. A handle or grip may also improve the users grip on the device should the linking component become slippery with a liquid or blood.

Secondary devices may be any device capable of being passed over a guidewire having a plurality of optical emitting fibers such as, but not limited to, a pass or exchange catheter, a balloon angioplasty device, a stent delivery device, an artherectomy catheter, a drug delivery device, and the like. Additionally, other devices such as, surgical instruments, optical imaging devices, and the like may be designed or redesigned to fit over a guidewire.

For example, in some embodiments, a physician may use a guidewire having a plurality of optical emitting fibers to inspect the walls of an artery. Upon discovering a lesion, the linking component may be easily disconnected from the guidewire and a secondary device, such as a catheter, may be placed over the guidewire to deliver a stent to injured tissue. The linking component may then be re-connected to the guidewire, enabling the user to use the optical emitting fibers to ensure proper placement of the stent before, during, or after deployment of the stent. During this process, the guidewire may be used to determine the length and type of stent to use prior to deployment of a stent. The rate of inflation of the balloon may be controlled as the stent is being deployed by using information obtained from the guidewire. Following stent deployment, the secondary device may be removed and the guidewire may be used to continue inspecting the artery.

In other embodiments, the secondary device may be used for drug delivery wherein the physician/user uses information obtained from the guidewire to determine how much of a drug to inject per unit time. In still other embodiments, the secondary device may be passed over the guidewire for interchange with still other devices or for manipulation by the physician/user. For example, in some embodiments, the guidewire and secondary device may be used in an artherectomy procedure (or other surgical cutting procedure) wherein information obtained using the guidewire may be used to determine where and how deeply to cut.

The embodiments described above offer numerous advantages including, for example, the accurate placement of a stent into a vessel lumen with reduced risk of stent over-expansion and artery rupture. Further, the accurate placement may reduce the risk of stent under-expansion and the incidence of late thrombosis. The systems and methods presented herein also allow for accurate placement and deployment of a stent or other device into a body cavity or vessel lumen based on determination of the size and shape of the lumen. As such, the stent placement may be controlled to allow for full deployment or partial deployment. The stent placement may also be controlled to allow for correct placement and deployment in irregularly shaped lumens, thus further reducing the risk of either over or under-expansion.

The invention also includes methods for making a connector 100 for a guidewire having a plurality of optical emitting fibers. The method may generally include the steps of assembling a guidewire having a plurality of optical emitting fibers, such that the plurality of optical emitting fibers may be at least equal to the total length of the guidewire probe and the linking component, and slicing the guidewire at an angle wherein the angled slice allows for realignment of the optical emitting fibers and for the guidewire to assume its original length. By slicing the guidewire having a plurality of optical emitting fibers, a guidewire probe and a linking component may be created, and in some embodiments, the slice may be skewed such that the guidewire probe created is longer than the linking component. In embodiments, the sliced optical emitting fibers may be ground and polished after slicing to improve the connection at the interface between the optical emitting fibers in the guidewire probe and the linking component. In other embodiments, a connector 100 may be fixed to the linking component at the interface between the guidewire probe and the linking component to hold the properly aligned interface in position during use.

In various embodiments, the method for making a connector 100 may include preparing a guidewire probe having any number of optical elements which allow for the transmission, shaping, or splitting of light propagated through the optical emitting fibers and may further include the preparation of a guidewire probe having other components or devices, such as, for example, bending elements, expanders, and flexible tips, which allow for proper and safe use of the guidewire probe.

In other embodiments, the method may include preparing a linking component having a connector connecting the linking component to other components such as, for example, an instrument box, a light source, an air compressor, detector, and the like. In still other embodiments, the method may include applying a material layer to the linking component which allows for improved gripping of the linking component by forming a handle or grip on the linking component.

In yet other embodiments, the guidewire probe may have a central wire or tube which may be manipulated to affect a change in the guidewire probe or attached device. In such embodiments, a hole or opening through which the central wire or tube may pass may be formed in the linking component. When die central wire is properly passed through the hole, the user of the guidewire probe may manipulate the central wire without disturbing the guidewire probe or the linking component.

The systems and methods presented herein integrate diagnostic techniques in the use of low coherence interferometry or other imaging systems to monitor the location of a lesion, and therapeutic techniques in the use of a balloon catheter system for the accurate placement and deployment of a stent at the location of a lesion. As such, the embodiments of the present disclosure eliminate the need for flushing solutions or other imaging enhancement methods that may be problematic to patient health. The expansion gas or fluid of the present system is delivered to the balloon, thus providing a cleared imaging field without introducing solutions into the body cavity or vessel lumen that may dilute the blood or other body fluid, potentially leading to ischemia, electrolyte imbalance or congestive heart failure.

The application of the present systems and methods in the field of cardiovascular therapy is only one of the possible applications for the present invention. Minimally invasive surgery is applied in many fields of medical diagnosis and therapy, such as, in other vascular, breast, urethral, renal, and abdominal procedures. The present invention may be applied in these fields.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub combination.

It will be appreciated by persons skilled in the art that the present invention is not limited to what has been particularly shown and described hereinabove. Rather the scope of the present invention is defined by the appended claims and includes both combinations and sub combinations of the various features described hereinabove, as well as variations and modifications thereof, which would occur to persons skilled in the art upon reading the foregoing description.

What is claimed is:

1. An optical probe comprising:
a guidewire comprising a plurality of optical emitting fibers, said guidewire having an angled proximal end and a distal end wherein light enters the plurality of optical emitting fibers at the angled proximal end and wherein light from the plurality of optical emitting fibers illuminates a target at the distal end;
a linking component having a plurality of optical fiber feed lines corresponding to each of the plurality of optical emitting fibers of the guidewire, said linking component having a proximal end and an angled distal end wherein the angled distal end of the linking component corresponds with the angled proximal end of the guidewire and wherein each of the plurality of optical fibers is aligned with a corresponding optical fiber feed line at a mating interface; and
a connector affixed to the distal end of the linking component and engagably attached to the proximal end of the guidewire wherein the connector locks the mating interface in place.

2. The optical probe of claim 1, wherein no part of the connector affixed to the guidewire exceeds a diameter of the guidewire.

3. The optical probe of claim 1, wherein the plurality of optical emitting fibers and optical fiber feed lines at the mating interface have a spatial and angular orientation that allows self alignment of each optical emitting fiber to its corresponding optical fiber feed line.

4. The optical probe of claim 1, wherein the connector comprises an attachment or appendage.

5. The optical probe of claim 1, wherein the plurality of optical emitting fibers and the optical fiber feed lines are selected from single mode fibers, multi-mode fibers, and combinations thereof.

6. The optical probe of claim 1, wherein the plurality of optical emitting fibers and the optical fiber feed lines comprise the same type of fiber.

7. The optical probe of claim 1, wherein the mating interface further comprises a fluid having a refractive index about equal to a refractive index of the plurality of optical emitting fibers and optical fiber feed lines.

8. An optical probe comprising:
a guidewire comprising at least one optical emitting fiber for observing a target;
a linking component for connecting and disconnecting the guidewire to a light source; and
a second device inserted over the guidewire that extends the length of the guidewire wherein the guidewire allows the second device to be positioned in the target area.

9. The optical probe of claim 8, wherein the second device delivers a treatment to diseased tissue observed by the at least one optical emitting fiber.

10. The optical probe of claim 8, wherein the second device further comprises a balloon.

11. The optical probe of claim 8, wherein the second device further comprises a balloon and a stent.

12. The optical probe of claim 8, wherein the linking component further comprises a connector affixed to an end of the linking component locking the guidewire and linking component in place.

13. A method for using an optical probe comprising:
    inserting a guidewire comprising a plurality of optical emitting fibers into a lumen wherein a distal end of the guidewire is inserted into the lumen and a proximal end of the guidewire remains outside of the lumen;
    connecting the guidewire to a light source and a processing device by a linking component comprising a plurality of optical fiber feed lines corresponding to each of the plurality of optical emitting fibers, said linking component having a proximal end and a distal end wherein the proximal end of the linking component engagably attaches to the proximal end of the guidewire;
    determining a position of diseased tissue within the lumen wherein the position of diseased tissue comprises a target position;
    maintaining a position of the guidewire close proximity to the target position;
    disconnecting the guidewire and the linking component;
    inserting a second device over the guidewire while the position of the guidewire is maintained in close proximity to the target position;
    utilizing the second device; and
    reconnecting the guidewire and the linking component.

14. The method of claim 13, wherein the component further comprises a connector for reversibly connecting the guidewire to the component having a mating interface wherein the plurality of optical emitting fibers and the corresponding plurality of optical fiber feed lines are ground and polished to an angle such that a spatial and angular orientation of the mating interface allows self alignment of each optical fiber feed fine to a corresponding optical emitting fiber.

15. The method of claim 13, wherein the second device is selected from a sleeve, a balloon, a stent and combinations thereof.

16. The method of claim 13, wherein utilizing the second device comprises deploying a stent in the target position.

17. The method of claim 16, further comprising inspecting placement of the stent using the guidewire following deployment of the stent to ensure proper placement and deployment.

18. A connector for a multi-fiber optical probe comprising:
    a guidewire comprising a plurality of optical emitting fibers, said guidewire having an angled proximal end and a distal end wherein light enters the plurality of optical emitting fibers at the angled proximal end and wherein light from the plurality of optical emitting fibers illuminates a target at the distal end;
    a linking component having a plurality of optical fiber feed lines corresponding to each of the plurality of optical emitting fibers, said linking component having a proximal end and an angled distal end wherein the angled distal end of the linking component corresponds with the angled proximal end of the guidewire and wherein each of the plurality of optical fibers is aligned with a corresponding optical fiber feed line at a mating interface; and
    a mating interface between the guidewire and the linking component.

\* \* \* \* \*